United States Patent [19]

Serboli et al.

[11] 4,182,804

[45] Jan. 8, 1980

[54] PREPARATION OF POLYMERS WHICH CONTAIN AMINE GROUPS OR SALTS THEREOF AND/OR QUATERNARY AMMONIUM GROUPS AND POLYMERS OBTAINED

[75] Inventors: Giancarlo Serboli, Saronno; Maurizio Straziota, Milan; Nicolina La Barba, San Donato Milanese, all of Italy

[73] Assignee: Anic S.p.A., Palermo, Italy

[21] Appl. No.: 847,426

[22] Filed: Nov. 1, 1977

[30] Foreign Application Priority Data

Nov. 11, 1976 [IT] Italy .................. 29235 A/76

[51] Int. Cl.$^2$ ................ C08F 8/30; C08F 8/32; C08F 8/36
[52] U.S. Cl. ........................... 525/56; 424/78; 424/79; 426/271; 521/32; 525/61; 536/30
[58] Field of Search ................ 526/9, 7, 8; 536/30; 521/32

[56] References Cited

U.S. PATENT DOCUMENTS

| | | | |
|---|---|---|---|
| 2,076,131 | 4/1937 | Rein | 526/9 |
| 2,081,528 | 5/1937 | Brodersen | 536/30 |
| 2,233,475 | 3/1941 | Dreyfus | 536/30 |
| 2,972,606 | 2/1961 | Hartman et al. | 526/9 |
| 3,304,297 | 2/1967 | Wegmann et al. | 526/9 |
| 3,345,346 | 10/1967 | Reynolds | 526/9 |
| 3,619,371 | 11/1971 | Crook et al. | 526/9 |
| 3,637,394 | 1/1972 | Smith et al. | 526/9 |
| 3,674,767 | 7/1972 | Lilly et al. | 526/9 |
| 3,684,784 | 8/1972 | Marze | 526/9 |
| 3,761,406 | 9/1973 | Tsuk | 526/9 |
| 3,976,621 | 8/1976 | Palladino et al. | 526/9 |

*Primary Examiner*—Stanford M. Levin
*Attorney, Agent, or Firm*—Morgan, Finnegan, Pine, Foley & Lee

[57] ABSTRACT

Polymers, such as ethylene-vinylacetate copolymer, polyvinyl alcohol or cellulose, containing amine groups or salts thereof or quaternary ammonium groups are disclosed. The polymers can be processed easily and display other interesting chemical properties such as having the particular chemical properties of the functional groups they contain. These polymers are prepared, generally by reacting a hydroxyl-containing polymer with a reactive compound which contains an available amine group.

12 Claims, No Drawings

PREPARATION OF POLYMERS WHICH CONTAIN AMINE GROUPS OR SALTS THEREOF AND/OR QUATERNARY AMMONIUM GROUPS AND POLYMERS OBTAINED

This invention relates to a method for the obtention of polymers which contain primary, secondary, tertiary amine groups, either free or a salt thereof, and quaternary ammonium groups, said polymers having satisfactory processability properties and being thus adapted to the production of artifacts.

The subject method consists in introducing said groups in a preformed polymer chain without substantially altering the properties of the starting polymer: more particularly, the method in question is based on the reaction of a polymer which contains hydroxyl groups, with compounds in which also the amine function is present, or with compounds which contain such groups as to be capable of reacting with the amines.

In general, the method of this invention consists in reacting hydroxyl-group containing polymers with compounds having the formula: X—R—Y, wherein R is selected from the group comprising alkylene radicals, substituted or unsubstituted benzene radicals and heterocyclic radicals, X is a member selected from the group comprising carboxyl radicals, sulfonic radicals, —COCl, and Y is a member selected from among amine, primary, secondary or tertiary groups, either free or a salt thereof. The compounds X.R.Y. can be pre-formed and introduced as such in the reaction environment, or, as an alternative, they can be originated in situ, in the presence of the hydroxylated polymer, by feeding the reaction with an amine and with a compound capable of binding the amine group and simultaneously reacting with the hydroxylated polymer. Conventional methods for the copolymerization of unsaturated amines with other monomers are known (Schildknecht, High Polymers, Vol.XVIII, 519-555 "Allyl amines and their salts").

Generally speaking, however, the unsaturated amines of the allylamine class and their derivatives do not polymerize satisfactorily, whereas the corresponding quaternary ammonium salts polymerize and copolymerize more readily within appropriate chemical systems and in the presence of free radicals.

However, the use of a few of these polymers and/or copolymers for the production of articles of manufacture has not been successful, as a rule, due to the poor processability of such polymers as caused by a not too high molecular weight and other inappropriate features.

Such polymers, conversely, have been used to produce paper having a high conductivity in the treatment of waters for the textile industries and for other uses.

There has been disclosed, inter alia, the copolymerization of unsaturated tertiary amines and quaternary ammonium salts with acrylonitrile (U.S. Pat. No. 2,631,995, U.S. Pat. No. 2,572,561, U.S. Pat. No. 2,617,781, German Pat. No. 963,475 and German Pat. No. 917,812).

Polymers which contain amine groups and/or quaternary ammonium group have also been described in "Ion-Containing Polymers", J. Polym. Sci., Symp., Vol. 45 (1974). The method according to the present invention is based on modification reactions of the hydroxyl groups contained in the polymer, specifically esterification and ether formation.

Esterification is carried out in the conventional way by using organic compounds which contain both the carboxyl and the aminic functions.

It is quite possible appropriately to use organic compounds which contain the carboxyl function and another group capable of subsequently reacting with the amines, such as —CH₂—X, wherein X is Cl, Br or I.

Compounds which lend themselves very well to this purpose are for example chloroacetic acid and 3-chloropropionic acid.

The ester group can also be introduced by reacting the polymeric alcohol or the alcoholates with the acidic chloride.

This latter reaction pattern has proven very interesting due to the high yields and the promptness of the reaction.

The reactions are preferably carried out in a homogeneous phase.

The solvents to be used are a function of the kind of polymer, but they are, as a rule, of the following types: saturated aliphatic hydrocarbons, aromatic hydrocarbons, cycloaliphatic hydrocarbons, halogen-substituted hydrocarbons, ethers, esters, ketones, alcohols and others.

The organic compounds which contain the acidic function and the aminic primary, secondary or tertiary function can be, by way of example:

(1) alpha . . . omega aminocacids, or, more generally,

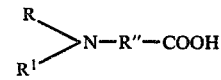

wherein R, R' are H, —CH₃, —C₂H₅ and others, R" is (—CH₂)ₙ and n ranges from 1 to 5.

(2) compounds which contain the amine, sulfonic, or sulfuric groups, of the kind:

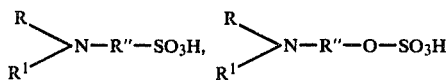

wherein R, R' are H, —CH₃, C₂H₅, R" is (—CH₂)ₙ, n being preferably 1 or 2.

(3) carboxylic acids of heterocyclic compounds containing nitrogen atoms, such as nicotinic and isonicotinic acid.

(4) chlorides-hydrochlorides of acids, with the basic groups described above.

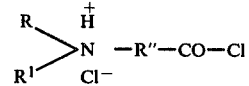

Polymers which contain hydroxyl groups are preferably obtained by hydrolyzing an ethylene-vinylacetate copolymer.

Other polymers which can be used are polyvinyl alcohol, cellulose and others.

The ethylene-vinyl acetate copolymers which can be used have a vinyl acetate contents ranging from 3% to 50% on a weight basis.

The hydrolysis is carried out, as a rule, in a homogeneous phase and comprises the steps of preparing a solution of the polymer in toluene, which is then treated with a solution of KOH in methanol and then refluxed until the hydrolysis has been completed.

The hydrolysis can also be carried out by using a solution of sodium methylate in methanol.

The obtention of polymers which contain quaternary ammonium groups takes place via the known quaternization reaction which consists in reacting the tertiary amine group with an alkyl halide, preferably methyl chloride, bromide or iodide, or with dimethyl sulfate.

Should the —OH groups of the polymer have been esterified with compounds which contain the group —CH$_2$X, wheren X is Cl, Br or I(such as 3-chloromethylbenzoyl chloride, 3-chloropropionic acid and others), the quaternary ammonium groups are obtained by a treatment with a tertiary amine, such as trimethylamine or triethylamine in a reaction medium which is preferably of the aprotic-polar genus, and in the presence of catalytic amounts of potassium iodide.

The polymers of the present invention have all the technological properties of the starting polymers, so that they can be moulded, extruded, shaped and treated, in general with the conventional techniques for giving any possible articles such as shaped profiles, fibres, fibrils, films and others. Since they contain special functional groups, they have the particular chemical properties thereof.

They can thus find quite special fields of use; as a matter of fact, those which contain free amine groups can be considered also as ion-exchange resins inasmuch as they, for their being basic, react with inorganic and organic acids to give the respective salts.

The polymers which contain free amine groups, or salt groups, or quaternary ammonium groups can adsorb anions, also of the polymeric type, in a stable manner, such as for example heparin, thus unfolding an anti-clotting action (non-thrombogenic polymers).

The amine groups which are present in the polymers referred to above, in addition, have proven to be capable of interacting with medicaments which contain acidic groups and thus they can afford a polymeric supporting member, under several forms, for medicaments of that kind.

A few examples are given hereinafter in order that the present invention may be more clearly understood, but no limitation is implied thereby.

EXAMPLE 1

A flask equipped with stirrer, thermometer and reflux condenser is charged with 800 mls. toluene and 50 grams of an ethylene-vinylacetate copolymer (I) which contains 26.3% of vinylacetate by weight. The mixture is heated with stirring until the polymer has completely been dissolved. There are added slowly, with stirring, 30 mls of a saturated solution of KOH in methanol and the mixture is refluxed during 3 hours approximately. Upon cooling, the hydrolyzed polymer (II) precipitates from the solution.

Upon filtration, washing with water and methanol to neutrality is carried out and the residue is dried in an oven at 60° C.

The infrared spectrum exhibits the band at about 3,400 cm$^{-1}$ due to the OH and the C=O band of vinyl acetate is totally absent, at 1,720 cm$^{-1}$. The content of —OH is 6% by weight, which corresponds to 15.5% of

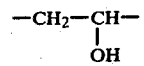

units, by weight. 20 grams of the hydrolyzed polymer (II) are completely dissolved in 400 mls toluene. Subsequently, there are added 7 grams of chloroacetic acid and 0.2 grams of p-toluenesulfonic acid. The mixture is heated to about 110° C. until the water as formed in the esterification reaction has completely been discharged. The polymer (III) is precipitated in methanol, washed with water and methanol and subsequently dried in an oven.

The chlorine content in the polymer is 9.2%, that which corresponds to an esterification yield of 95%. 10 grams of the polymer (III) are solubilized in 200 mls toluene at the temperature of about 70° C. Methanol is added in such an amount as not to cause the precipitation of the polymer (about 50 mls) and 20 mls diethylamine are also added. The mixture is heated to 50° C. during 12 hours. The excess diethylamine is discharged by evaporating off it under reduced pressures.

From a small amount of the polymer solution, the polymer (IV) is precipitated in nor.heptane, washed with methanol and oven dried. The nitrogen value is 2.7%, that which corresponds to a yield of 86%. The solution in toluene of the polymer (IV), which contains methanol, is supplemented with 10 grams of methyl iodide. The mixture is heated to 40° C. with stirring for about 48 hours. On completion of the reaction, methanol and the excess methyl iodide are recovered by evaporation under reduced pressures. The polymer (V) is precipitated in nor.heptane, washed with water and acetone and oven dried. The content of iodine is 18.4%, which corresponds to a yield of 96%.

Inasmuch as the several reaction intermediates have not been separated or purified, the yields of the several reaction steps have been calculated on the basis of the contents of -OH, Cl, N, and I, as determined experimentally.

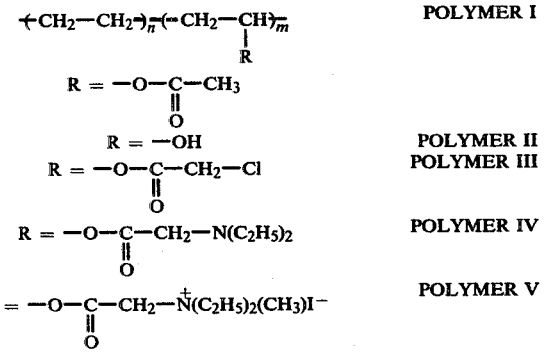

EXAMPLE 2

10 grams of the hydrolyzed polymer (II) described in Example 1 and containing the 6% by weight of -OH, are dissolved in hot condition (90° C.-110° C.) in 200 mls toluene. There are added 2.2 grams of 80% NaH in paraffin oil and, on completion of the evolution of hydrogen, 7 grams of nicotinoyl chloride hydrochloride are added. Evolution of hydrogen is experienced again. The mass is stirred at 90° C.-110° C. during 4 to 5 hours. As the reaction is over, the polymer is precipitated in methanol, or nor.heptane and collected on a filter, washed with methanol, water and acetone, and oven dried. The nitrogen content in the polymer is 3.1% which corresponds to a yield of 87%.

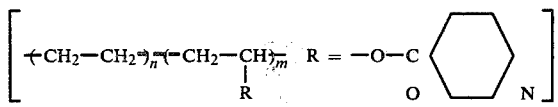

5 grams of the esterified polymer are dissolved at 60° C.–70° C. in 100 mls toluene. There are added 20 mls methanol and 3 grams of methyl iodide. The mixture is heated to 40° C. with stirring during about 48 hours. On completion of the reaction, methanol and the excess methyl iodide are removed by evaporation under reduced pressures and the polymer is precipitated in nor.-heptane. The polymer is collected on a filter, washed with acetone and methanol and oven dried. The iodine content in the polymer is 17.8%, which corresponds to a yield of 86%.

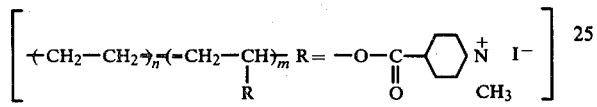

EXAMPLE 3

10 grams of hydrolyzed polymer (II) are dissolved at 90° C.–110° C. in 200 mls of toluene. There are added, in two increments, 5 grams of KOH, 6 grams of 1-chloro-2-dimethylamino-ethane hydrochloride and 0.3 grams of KI. The mixture is refluxed during 20 hours. The polymer is precipitated in methanol, then washed with water and methanol and oven dried. The nitrogen content in the polymer is 2.5% which corresponds to a yield of 64%.

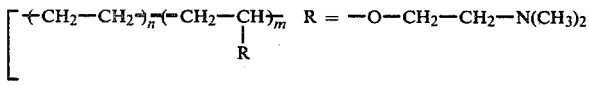

EXAMPLE 4

10 grams of the polymer (IV) as prepared according to the procedure described in Example 1 are dissolved in 200 mls of hot toluene. There are added 50 mls of methanol and 5 mls of 37%-HCl and the mixture is heated to 60° C.–70° C. during one hour. Upon cooling the solution at room temperature, the polymer precipitates. The polymer is collected on a filter, washed with water and methanol and oven dried. The nitrogen content of the polymer is 2.9% and that of chlorine is 7.3%. Yield 90%.

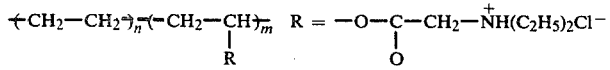

EXAMPLE 5

10 grams of the hydrolyzed polymer (II) of Example 1 are dissolved in 200 mls of hot xylene. There are added 7 grams of 3-chloromethylbenzoyl chloride and the mixture is refluxed with stirring during 8 hours approximately. From a portion of the solution the polymer is precipitated in methanol. The precipitate is washed with methanol and acetone and oven dried. The chlorine content in the polymer is 7.2% corresponding to a yield of 90%. To the remaining solution there are added about 50 mls of N,N-dimethylformamide (dimethylsulfoxide can also be used), 0.1 gram of potassium iodide and 7 grams of triethylamine. The mixture is heated with stirring to 80° C. during about 8 hours. The polymer is precipitated in methanol, washed with methanol and acetone and oven dried. The nitrogen content in the polymer is 1.97% and the chlorine content is 5.2%; the yield is 84%.

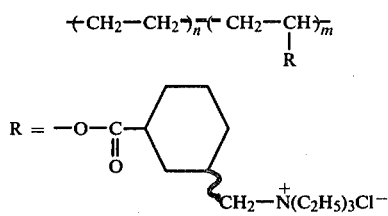

EXAMPLE 6

A film of the polymer (IV) described in Example 1, having a thickness of 0.1 millimeter and obtained by moulding, is immersed during 12 hours in a water/methanol (1:1) solution containing 0.5% of sodium heparinate (pH of the solution 5–6). The film is then washed a number of times with distilled water so as to remove the heparine which has not been fixed. The determination of sulfur indicates a concentration of heparine on the surface equal to 0.06 milligram per square centimeter.

EXAMPLE 7

10 grams of the polymer (IV) prepared according to the procedure of Example 1 are dissolved in 200 mls of a hot mixture of toluene and ethanol, containing 25% of the alcohol. There are added 5 grams of undecylenic acid, previously dissolved in the minimum quantity of alcohol necessary and the mixture is refluxed during 6 hrs. approx. About the fourth portion of the solution is treated with methanol to precipitate the polymer: the latter is then collected on a filter, washed with methanol and oven dried in a vacuo at 60° C. The analysis of the double bonds of the undecylenic acid bound to the polymer indicates a content of such acid in the polymer of 19%. In the solution of the remaining polymer there has been immersed a gauze fabric for about one hour. The fabric has then been oven dried in a vacuo at 60° C., washed subsequently with ethanol and dried again in an oven in a vacuo. The thus-prepared gauze has proven to be effective in the local treatment of mycoses.

EXAMPLE 8

10 grams of the polymer (IV) prepared according to the procedure of Example 1 are dissolved in 200 mls of a hot mixture of toluene and methanol, containing the 25% of the alcohol. There are added 4 grams of sorbic acid which had previously been dissolved in a small amount of methanol, and the mixture is refluxed during 6 hours approximately. A portion of the solution has been precipitated with methanol, in order to separate the solid polymer, which has then been collected on a filter, washed with methanol and oven dried in a vacuo at 60° C. On the thus-obtained polymer the content of sorbic acid has been determined, and this was in the order of magnitude of 13%. The remaining polymeric solution has been employed for spray-coating the interior of a PVC cylindrical container so as to produce on the internal surface of the container a thin and even polymer film. The container has then been subjected to vacuum drying so as to remove the solvent (oven in a vacuo at 60° C.). In the thus-coated container, and in two PVC containers (untreated) there have been introduced equal volumes of fruit juices prepared according to the usual procedures and to which no preservative additions had been made. The containers have been sealed and stored in a thermostat at 30° C. during three months. After this time, the fruit juice contained in the uncoated vessels exhibited changes of colour and viscosity (a sign of alteration) and modification in the taste were also detected.

On the contrary, the fruit juice contained in the vessel coated with the sorbic-acid-containing polymer film was unaltered both as to its appearance and its taste.

We claim:

1. A method for producing a polymer which contains free primary, secondary or tertiary amine groups or salts thereof and/or quaternary ammonium groups, the polymer having good processability characteristics, which method consists essentially of the step of:

reacting a polymer containing at least one hydroxyl group in the polymer with an organic compound containing both an acidic and an amine group, said hydroxyl-containing polymer selected from the group consisting of an ethylenevinylacetate copolymer with a vinylacetate content between 3% and 50% by weight which has been partially hydrolyzed and polyvinyl alcohol, said organic compound selected from the group consisting of:

(a) 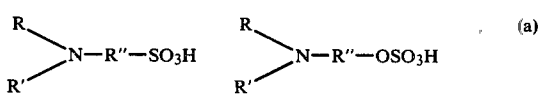

wherein R, R' are H, or alkyl and R" is (—CH₂) n, n being 1 or 2.

(b) carboxylic acids of heterocyclic compounds containing one nitrogen atom; and (c) chlorides-hydrochlorides of acids, with the basic groups described above having the formula:

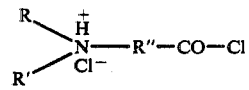

wherein R, R' are H, or alkyl and R" is (—CH₂)n, n being an integer between 1 and 5.

2. A method as defined in claim 1 wherein said hydroxyl group containing polymer is said ethylene-vinylacetate.

3. A method as defined in claim 1 wherein said hydroxyl group containing polymer is polyvinyl alcohol.

4. A method as defined in claim 1 wherein said organic compound is:

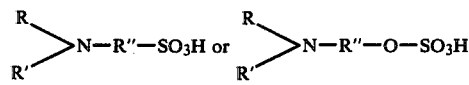

wherein R, R' are H, or alkyl and R" is (—CH₂)ₙ, n being 1 or 2.

5. A method as defined in claim 1 wherein said organic compound is a carboxylic acid of a heterocyclic compound containing one nitrogen atom.

6. A method as defined in claim 5 wherein said organic compound is nicotinic acid or isonicotinic acid.

7. A method as defined in claim 1 wherein said organic compound is:

a chloride-hydrochloride of an acid having the formula:

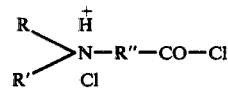

wherein R, R' are H, or alkyl and R" is (—CH₂)n, n being an integer between 1 and 5.

8. A method as defined in claim 2 wherein said organic compound is:

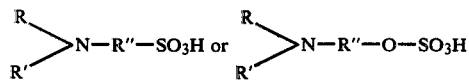

wherein R, R' are H or alkyl, and R" is (—CH₂)n, n being 1 or 2.

9. A method as defined in claim 2 wherein said organic compound is a carboxylic acid of a heterocyclic compound containing one nitrogen atom.

10. A method as defined in claim 2 wherein said organic compound is nicotinic acid or isonicotinic acid.

11. A method as defined in claim 2 wherein said organic compound is:

a chloride-hydrochloride of an acid having the formula:

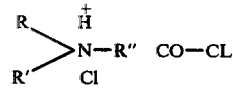

wherein R, R' are H or alkyl, and R" is (—CH₂)n, n being an integer between 1 and 5.

12. A polymer produced according to the method of claim 1.

* * * * *